United States Patent
Kopetsch et al.

(10) Patent No.: US 10,364,202 B2
(45) Date of Patent: Jul. 30, 2019

(54) METHANOL SYNTHESIS FROM SYNTHESIS GASES WITH HYDROGEN DEFICIENCY

(71) Applicant: L'Air Liquide, Societe Anonyme pour l'Etude et l'Exploitation des Procedes Georges Claude, Paris (FR)

(72) Inventors: Hans Kopetsch, Bad Homburg (DE); Veronika Gronemann, Karben (DE); Tobias Oelmann, Bad Vilbel (DE)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 16/085,112

(22) PCT Filed: Mar. 6, 2017

(86) PCT No.: PCT/EP2017/025036
§ 371 (c)(1),
(2) Date: Sep. 14, 2018

(87) PCT Pub. No.: WO2017/157530
PCT Pub. Date: Sep. 21, 2017

(65) Prior Publication Data
US 2019/0077735 A1   Mar. 14, 2019

(30) Foreign Application Priority Data
Mar. 16, 2016   (EP) .................................... 16400006

(51) Int. Cl.
*C07C 29/152*    (2006.01)
*B01J 8/02*    (2006.01)
(Continued)

(52) U.S. Cl.
CPC .......... *C07C 29/152* (2013.01); *B01D 53/047* (2013.01); *B01D 53/229* (2013.01);
(Continued)

(58) Field of Classification Search
CPC ... C07C 29/152; C07C 29/1518; C07C 31/04; B01D 53/047; B01D 53/229;
(Continued)

(56) References Cited

U.S. PATENT DOCUMENTS

2009/0018220 A1   1/2009   Fitzpatrick

FOREIGN PATENT DOCUMENTS

| DE | 2 934 332 | 3/1981 |
| EP | 0 790 226 | 4/2000 |
| EP | 1 016 643 | 7/2000 |

OTHER PUBLICATIONS

International Search Report and Written Opinion for PCT/EP2017/025036, dated May 29, 2017.

*Primary Examiner* — Lessanework Seifu
(74) *Attorney, Agent, or Firm* — Justin K. Murray

(57) ABSTRACT

The invention relates to a process and a plant for the methanol synthesis, in particular for the methanol synthesis from a synthesis gas which has a hydrogen deficiency. According to the invention, a purge gas stream therefor is branched off from the synthesis gas circuit of the methanol synthesis, liberated from methanol traces in a washing device, and then treated in a hydrogen separation device which comprises a membrane separation stage and a pressure swing adsorption stage. Depending on the application and magnitude of the hydrogen deficit the membrane separation stage and the pressure swing adsorption stage can be connected in series or in parallel.

19 Claims, 2 Drawing Sheets

(51) Int. Cl.
*B01D 53/22* (2006.01)
*C07C 29/156* (2006.01)
*B01J 7/00* (2006.01)
*B01J 19/00* (2006.01)
*B01D 53/047* (2006.01)
*C07C 29/151* (2006.01)
*C07C 31/04* (2006.01)

(52) U.S. Cl.
CPC ............... *B01J 7/00* (2013.01); *B01J 8/0278* (2013.01); *B01J 19/0053* (2013.01); *C07C 29/156* (2013.01); *C07C 29/1518* (2013.01); *B01J 2219/00452* (2013.01); *B01J 2219/00479* (2013.01); *B01J 2219/00594* (2013.01); *C07C 31/04* (2013.01)

(58) Field of Classification Search
CPC .................. B01J 8/0278; B01J 19/0053; B01J 2219/00452; B01J 2219/00479; B01J 2219/00594

See application file for complete search history.

METHANOL SYNTHESIS FROM SYNTHESIS GASES WITH HYDROGEN DEFICIENCY

CROSS REFERENCE TO RELATED APPLICATIONS

This application is a § 371 of International PCT Application PCT/EP2017/025036, filed Mar. 6, 2017, which claims the benefit of EP16400006.9, filed Mar. 16, 2016, both of which are herein incorporated by reference in their entireties.

FIELD OF THE INVENTION

The present invention relates to a process and a plant for the methanol synthesis, in particular for the methanol synthesis from a synthesis gas which has a hydrogen deficiency.

BACKGROUND

Processes for the production of methanol by catalytic conversion of synthesis gas containing hydrogen and carbon oxides have long since been known to those skilled in the art. For example in Ullmann's Encyclopedia of Industrial Chemistry, Sixth Edition, 1998 Electronic Release, Chapter "Methanol", Sub-chapter 5.2 "Synthesis", various basic processes for the production of methanol are described.

A more advanced, two-stage process for the production of methanol is known for example from EP 0 790 226 B1. Methanol accordingly is produced in a cyclic process in which a mixture of fresh and partly reacted synthesis gas first is supplied to a water-cooled reactor and then to a gas-cooled reactor, in each of which the synthesis gas is converted to methanol on a copper-based catalyst. The methanol produced in the process is separated from the synthesis gas to be recirculated, which then is countercurrently guided through the gas-cooled reactor as coolant and preheated to a temperature of 220 to 280° C., before it is introduced into the first synthesis reactor. A part of the synthesis gas to be recirculated is removed from the process as purge stream (so-called purge), which is small as compared to the gas inventory present in the system, in order to prevent that inert components, impurities or by-products accumulate within the synthesis gas circuit. This measure also is taught in the unexamined German Patent Application DE 2934332 A1 and in the European Patent Application EP 1016643 A1.

This process however requires that the stoichiometric number (R) of the synthesis gas used, defined by the formula:

$$R=([H_2]-[CO_2])/([CO]+[CO_2]),$$

with [x]=concentration of the component x, is at least 2, that the synthesis gas used hence contains enough hydrogen with regard to the production of methanol. Synthesis gases with hydrogen deficiency, on the other hand, can be obtained from reforming processes which include a stage of partial oxidation, such as the autothermal reformation (ATR). In such a case the hydrogen is consumed in the methanol synthesis reaction, while a major part of the carbon oxides is left unreacted, which leads to a composition in the synthesis loop which has a high content of carbon oxides, but is poor in hydrogen, i.e. has a hydrogen deficit or a hydrogen deficiency. This has various consequences, which include the fact that the required catalyst volume is high and that the fraction of by-products (in particular higher alcohols and ketones) is distinctly higher than normal.

It is known per se to supply hydrogen from other sources to the synthesis gas deficient in $H_2$, in order to bring the stoichiometric number into the optimal range of 2 or higher. As hydrogen source the purge stream can be used, among other things, which still has a content of non-converted hydrogen that can be separated by means of a hydrogen recovery unit. The typical hydrogen concentration in the purge stream is about 70 vol-%. Another alternative consists in recovering hydrogen from a side stream of the fresh synthesis gas, which also is referred to as make-up gas (MUG), and to feed this hydrogen back into the synthesis gas. The laid-open US patent application US 2009/0018220 A1 teaches a methanol synthesis process in which hydrogen is obtained from at least a part of said purge gas and a part of said make-up gas, wherein the recovered hydrogen is introduced into the synthesis gas mixture. The hydrogen recovery units used include the pressure swing adsorption (PSA) or—as an alternative—the $H_2$ separation by means of a membrane.

The disadvantage of this arrangement, however, consists in that within the hydrogen recovery unit a part of the hydrogen gets lost, before at all reaching the synthesis loop. In addition, when the synthesis gas make-up gas stream already contains a hydrogen deficit, the same only is increased by additional separation of $H_2$ from a make-up gas side stream. Due to the separation of $H_2$ from the make-up gas side stream, a waste stream containing CO and $CO_2$ then is obtained in the hydrogen recovery unit, wherein the carbon oxides of the methanol synthesis contained therein get lost.

SUMMARY OF THE INVENTION

Certain embodiments of the present invention provide a methanol synthesis process which is able to process synthesis gas with a hydrogen deficiency, without having the described disadvantages of the prior art.

This is solved by a process and by a plant with the features as described herein.

Process According to an Embodiment of the Invention:

A process for producing methanol from a synthesis gas containing hydrogen, carbon oxides and optionally inert components, comprising the following steps:

(a) providing a synthesis gas make-up gas stream containing hydrogen, carbon oxides and optionally inert components, which contains a hydrogen deficit with respect to the stoichiometry specified for the methanol synthesis, (b) combining the synthesis gas make-up gas stream deficient in hydrogen with a trimming gas stream containing hydrogen to obtain a synthesis gas make-up gas stream enriched in hydrogen, (c) combining the synthesis gas make-up gas stream enriched in hydrogen with the synthesis gas cycle gas stream obtained in step (g) to obtain a synthesis gas feed gas stream, (d) introducing the synthesis gas feed gas stream into at least one methanol synthesis reactor and at least in part catalytically converting the carbon oxides contained in the synthesis gas feed gas stream with hydrogen under methanol synthesis conditions to obtain methanol, (e) discharging a product gas stream containing methanol vapor and non-converted synthesis gas constituents from the at least one methanol synthesis reactor, (f) at least partly separating the methanol from the product gas stream by cooling and condensation, (g) fractionating the product gas stream after separation of the methanol into a synthesis gas cycle gas stream and a purge gas stream loaded with methanol residues, recirculating the synthesis gas cycle gas stream to step (c),
(h) introducing the purge gas stream loaded with methanol residues into a washing device, contacting the purge gas stream loaded with methanol residues in the washing device with a washing agent, preferably water, discharging a purge gas stream depleted of methanol and a washing agent loaded with methanol from the washing device,
(i) introducing the purge gas stream depleted of methanol into a hydrogen separation device which comprises a membrane separation stage and a pressure swing adsorption stage, wherein at least one gas stream enriched in hydrogen and at least one gas stream depleted of hydrogen is obtained,
(j) recirculating at least one gas stream enriched in hydrogen as trimming gas stream containing hydrogen to step (b).

Plant According to an Embodiment the Invention:

A plant for producing methanol from a synthesis gas containing hydrogen, carbon oxides and optionally inert components, comprising the following plant components:
(a) a synthesis gas generation stage for providing a synthesis gas make-up gas stream containing hydrogen, carbon oxides and optionally inert components, which contains a hydrogen deficit with respect to the stoichiometry specified for the methanol synthesis,
(b) a first mixing device for combining the synthesis gas make-up gas stream deficient in hydrogen with a trimming gas stream containing hydrogen to obtain a synthesis gas make-up gas stream enriched in hydrogen,
(c) a second mixing device for combining the synthesis gas make-up gas stream enriched in hydrogen with a synthesis gas cycle gas stream to obtain a synthesis gas feed gas stream,
(d) at least one methanol synthesis reactor, a conduit for introducing the synthesis gas feed gas stream into the at least one methanol synthesis reactor,
(e) a conduit for discharging a product gas stream containing methanol vapor and non-converted synthesis gas constituents from the at least one methanol synthesis reactor,
(f) a separating device for at least partly separating the methanol from the product gas stream by cooling and condensation,
(g) a fractionating device for fractionating the product gas stream after separation of the methanol into a synthesis gas cycle gas stream and a purge gas stream loaded with methanol residues, and a conduit for recirculating the synthesis gas cycle gas stream to the second mixing device,
(h) a washing device, a conduit for introducing the purge gas stream loaded with methanol residues into the washing device, a conduit for introducing the washing agent, a conduit for discharging a purge gas stream depleted of methanol from the washing device, and a conduit for discharging a washing agent loaded with methanol from the washing device,
(i) a hydrogen separation device, comprising a membrane separation stage and a pressure swing adsorption stage, a conduit for introducing the purge gas stream depleted of methanol into the hydrogen separation device, a conduit for discharging a gas stream enriched in hydrogen from the hydrogen separation device, and a conduit for discharging a gas stream depleted of hydrogen from the hydrogen separation device,
(j) a conduit for recirculating a gas stream enriched in hydrogen as trimming gas stream containing hydrogen to the first mixing device.

The conversion conditions or methanol synthesis conditions required for the conversion of synthesis gas to methanol are known to the skilled person from the prior art, for example from the documents discussed above. Necessary adaptations of these conditions to the respective operating requirements will be made on the basis of routine experiments.

Fluid connection between two regions of the plant according to the invention is understood to be any kind of connection which enables a fluid, for example a gas stream, to flow from the one to the other of the two regions, regardless of any interposed regions or components.

The water used as washing agent mostly is demineralized water. However, other water qualities, in particular those of higher purity, for example high-purity water or distilled water, can also be used as washing agent. Water of lower purity can be used as washing agent when the accompanying substances present create no problems in downstream process stages.

The use of a hydrogen separation device, comprising a membrane separation stage and a pressure swing adsorption stage, provides for an efficient separation of the hydrogen required for adjusting the desired stoichiometric number. The waste streams obtained can be used further, for example as fuel gas within the reformer plant upstream of the methanol synthesis or as heating gas or fuel gas in an apparatus for steam generation. A material use of the waste streams, for example in an adjacent plant for coal gasification, also is possible. The inventive liberation of the purge gas stream from methanol residues in the washing device advantageously cooperates with the hydrogen separation device, as its service life is increased: Methanol residues in the purge gas otherwise would damage the membrane of the membrane separation stage or occupy a part of the adsorption capacity of the adsorbent used in the pressure swing adsorption stage.

The combination of membrane separation and pressure swing adsorption (PSA) leads to a technically and economically expedient hydrogen separation: The use of a PSA leads to high-purity hydrogen (purity 99.9 vol-%) at a recovery of about 80% of the hydrogen in the gas to be separated. However, this is a relatively complicated and cost-intensive technique. On the other hand, the membrane separation leads to a lower purity of the separated hydrogen (about 80 to 90 vol-% in the permeate) at a recovery of about 70% of the hydrogen from the purge gas, but this is a relatively simple and inexpensive technique.

Coupling of said separation processes therefore leads to the optimum utilization of the advantages and the saving of costs as well as to a high flexibility with regard to the application: When the amount of hydrogen to be recirculated is to be maximized, a serial interconnection of the membrane separation stage with downstream PSA can be considered. On the other hand, when a part of the separated high-purity hydrogen is to be exported to consumers outside the process, a parallel connection of membrane separation stage and PSA can be expedient. The high-purity hydrogen then exclusively is taken from the PSA and supplied to the external consumer.

Preferred Aspects of the Invention

In a preferred aspect of the process according to the invention the membrane separation stage and the pressure swing adsorption stage are connected in series in the hydrogen separation device and are in fluid connection with each other. As already explained above, this procedure is recommendable when the amount of hydrogen to be recirculated is to be maximized.

Another preferred aspect of the process according to the invention is characterized in that in the hydrogen separation device first the membrane separation stage and then the pressure swing adsorption stage are traversed by the purge gas stream depleted of methanol. In this way, a pre-separation is effected in the comparatively unselectively operating membrane separation stage and the fine separation is effected in the highly selectively operating pressure swing adsorption stage, wherein the latter then only is loaded with a smaller volume flow and thus can be designed smaller.

In a development of the above-discussed aspect of the process according to the invention a first gas stream enriched in hydrogen is obtained as permeate in the membrane separation stage, which as trimming gas stream is combined with the synthesis gas make-up gas stream deficient in hydrogen. The relatively low hydrogen purity in the permeate often already is sufficient for an adjustment of the desired stoichiometric number in the synthesis gas feed gas stream, in particular when the hydrogen deficit only is small.

In a further development of the above-discussed aspect of the process according to the invention the retentate obtained in the membrane separation stage is charged to the pressure swing adsorption stage, and in the pressure swing adsorption stage a second gas stream enriched in hydrogen is obtained, which as trimming gas stream is combined with the synthesis gas make-up gas stream deficient in hydrogen or is discharged from the process as hydrogen export stream. A use as further trimming gas stream above all provides certain advantages when the synthesis gas feed gas stream has a larger hydrogen deficit. Otherwise, the gas stream enriched in hydrogen, which is obtained in the pressure swing adsorption stage, can be supplied to external consumers as hydrogen export stream.

In the aspect of the process according to the invention as discussed above it is preferred particularly when the second gas stream enriched in hydrogen is combined first with the first gas stream enriched in hydrogen and subsequently as trimming gas stream with the synthesis gas make-up gas stream deficient in hydrogen. In this way, a homogeneous condition of the trimming gas stream and the synthesis gas make-up gas stream enriched in hydrogen is achieved.

In an alternative aspect of the process according to the invention the membrane separation stage and the pressure swing adsorption stage are connected in parallel in the hydrogen separation device, wherein a part of the purge gas stream depleted of methanol is charged to the membrane separation stage and the remaining part of the purge gas stream depleted of methanol is charged to the pressure swing adsorption stage. As already explained above, this procedure is recommendable when a part of the high-purity hydrogen separated by means of PSA is to be exported to consumers outside the process.

In a development of the above-discussed aspect of the process according to the invention a first gas stream enriched in hydrogen is obtained as permeate in the membrane separation stage, which as trimming gas stream is combined with the synthesis gas make-up gas stream deficient in hydrogen. The relatively low hydrogen purity in the permeate often already is sufficient for an adjustment of the desired stoichiometric number in the synthesis gas feed gas stream, in particular when the hydrogen deficit only is small.

In a further aspect of the process according to the invention a second gas stream enriched in hydrogen is obtained in the pressure swing adsorption stage, which as trimming gas stream is combined with the synthesis gas make-up gas stream deficient in hydrogen or is discharged from the process as hydrogen export stream. A use as further trimming gas stream above all provides certain advantages when the synthesis gas feed gas stream has a larger hydrogen deficit. Otherwise, the gas stream enriched in hydrogen, which is obtained in the pressure swing adsorption stage, can be supplied to external consumers as hydrogen export stream.

In a further aspect of the invention the provision of the synthesis gas make-up gas stream is effected by means of a synthesis gas generation stage which comprises an autothermal reformer. The synthesis gas make-up gas stream obtained in this way often has a hydrogen deficit, as due to the oxidative reaction conditions in the autothermal reformer a part of the hydrogen formed gets lost by combustion.

In a particular aspect of the plant according to the invention the same is characterized in that in the hydrogen separation device the membrane separation stage and the pressure swing adsorption stage are connected in series and are in fluid connection with each other. As already explained above, this procedure is recommendable when the amount of hydrogen to be recirculated is to be maximized.

Another preferred aspect of the plant according to the invention is characterized in that in the hydrogen separation device first the membrane separation stage and then the pressure swing adsorption stage are traversed by the purge gas stream depleted of methanol. In this way, a pre-separation is effected in the comparatively unselectively operating membrane separation stage and the fine separation is effected in the highly selectively operating pressure swing adsorption stage, wherein the latter then only is loaded with a smaller volume flow and thus can be designed smaller.

In a development of the above-discussed aspect of the plant according to the invention the same also comprises a conduit with which a first gas stream enriched in hydrogen, which is obtained as permeate in the membrane separation stage, is recirculated to the first mixing device as trimming gas stream. The relatively low hydrogen purity in the permeate often already is sufficient for an adjustment of the desired stoichiometric number in the synthesis gas feed gas stream, in particular when the hydrogen deficit only is small.

In a further development of the above-discussed aspect of the plant according to the invention the same also comprises a conduit for introducing the retentate obtained in the membrane separation stage into the pressure swing adsorption stage and a conduit for introducing a second gas stream enriched in hydrogen, which is obtained in the pressure swing adsorption stage, as trimming gas stream into the first mixing device or for discharging from the plant as hydrogen export stream. A use as further trimming gas stream above all provides certain advantages when the synthesis gas feed gas stream has a larger hydrogen deficit. Otherwise, the gas stream enriched in hydrogen, which is obtained in the pressure swing adsorption stage, can be supplied to external consumers as hydrogen export stream.

It is preferred particularly in the above-discussed aspect of the plant according to the invention when it furthermore comprises a mixing device for combining the second gas stream enriched in hydrogen with the first gas stream enriched in hydrogen, and a conduit for supplying the mixed gas stream obtained to the first mixing device. In this way, a homogeneous condition of the trimming gas stream and the synthesis gas make-up gas stream enriched in hydrogen is achieved.

In an alternative aspect of the plant according to the invention the membrane separation stage and the pressure swing adsorption stage are connected in parallel in the hydrogen separation device, and the plant furthermore comprises a conduit for introducing a part of the purge gas stream depleted of methanol into the membrane separation stage and a conduit for introducing the remaining part of the purge gas stream depleted of methanol into the pressure swing adsorption stage. As already explained above, this aspect is recommendable when a part of the high-purity hydrogen separated by means of PSA is to be exported to consumers outside the process.

In a development of the above-discussed aspect of the plant according to the invention the same furthermore comprises a conduit with which a first gas stream enriched in hydrogen, which is obtained as permeate in the membrane separation stage, is recirculated to the first mixing device as trimming gas stream. The relatively low hydrogen purity in the permeate often already is sufficient for an adjustment of the desired stoichiometric number in the synthesis gas feed gas stream, in particular when the hydrogen deficit only is small.

In a further development of the above-discussed aspect of the plant according to the invention the same also comprises a conduit for introducing a second gas stream enriched in hydrogen, which is obtained in the pressure swing adsorption stage, as trimming gas stream into the first mixing device or for discharging from the plant as hydrogen export stream. A use as further trimming gas stream above all provides certain advantages when the synthesis gas feed gas stream has a larger hydrogen deficit. Otherwise, the gas stream enriched in hydrogen, which is obtained in the pressure swing adsorption stage, can be supplied to external consumers as hydrogen export stream.

BRIEF DESCRIPTION OF THE DRAWINGS

Further features, advantages and possible applications of the invention can also be taken from the following description of exemplary embodiments and numerical examples as well as the drawings. All features described and/or illustrated form the subject-matter of the invention per se or in any combination, independent of their inclusion in the claims or their back-reference.

In the drawings.

DETAILED DESCRIPTION OF THE INVENTION

Figure 1:
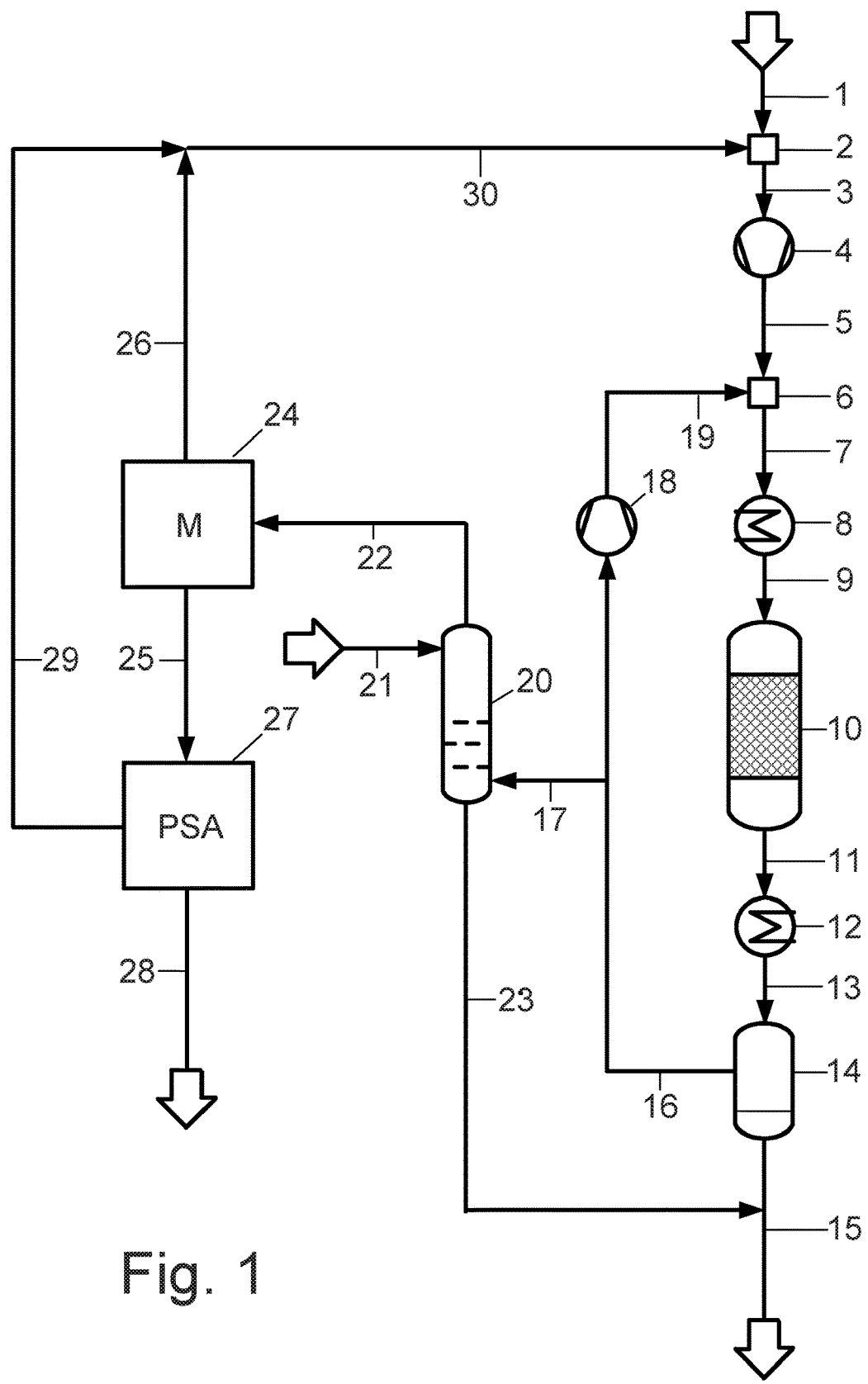
FIG. 1 shows the schematic representation of the process of the invention and the plant of the invention according to a first aspect.

In FIG. 1 the process of the invention and the plant of the invention according to a first aspect is explained, whose objective is the maximum recovery of hydrogen from the purge gas of the methanol synthesis.

Via conduit 1, a synthesis gas make-up gas stream containing hydrogen and carbon oxides, which contains a hydrogen deficit with respect to the stoichiometry specified for the methanol synthesis, is guided to a first mixing device 2. In the first mixing device 2 the synthesis gas make-up gas stream deficient in hydrogen is combined with a trimming gas stream containing hydrogen, which via conduit 30 is guided to the first mixing device, to obtain a synthesis gas make-up gas stream enriched in hydrogen. Via conduit 3, the same is guided to the compressor 4 and compressed there to the synthesis pressure of the methanol synthesis.

Via conduit 5, the compressed synthesis gas make-up gas stream enriched in hydrogen is guided to the second mixing device 6 and combined there with the synthesis gas cycle gas stream supplied via conduit 19 to obtain a synthesis gas feed gas stream. Via conduit 7, the synthesis gas make-up gas stream is guided to the heating device 8 and heated there to the reaction temperature of the methanol synthesis. The heating device 8 preferably comprises a heat exchanger with which the thermal energy dissipated upon cooling of the product stream of the methanol synthesis reactor is at least partly transmitted to the synthesis gas feed gas stream entering into the reactor. The synthesis gas feed gas stream is heated to a temperature between 180 and 280° C., preferably between 190 and 250° C.

Via conduit 9, the synthesis gas feed gas stream heated to the reaction temperature of the methanol synthesis is introduced into the methanol synthesis reactor 10. In the same the carbon oxides contained in the synthesis gas feed gas stream partly are catalytically converted to methanol by using hydrogen under methanol synthesis conditions. The methanol synthesis reactor can consist of an interconnection of several individual reactors, which for example are gas-cooled or water-cooled, as is taught by the document EP 0 790 226 B1.

The product stream which comprises methanol formed in the methanol synthesis reactor and non-converted synthesis gas constituents, leaves the methanol synthesis reactor via conduit 11, is cooled in the cooler 12, and by means of conduit 13 guided to the phase separation device 14. As already indicated above, the cooler can comprise a heat exchanger, wherein the thermal energy to be dissipated is transmitted to the cold synthesis gas feed gas stream by indirect heat exchange, and the latter thus is heated.

In the phase separation device 14 the cooled product stream of the methanol synthesis reactor is fractionated into a liquid phase and into a gas phase. The obtained liquid phase contains produced methanol and water as coupling product; via conduit 15, it is guided to a non-illustrated distillation device in which methanol and water are separated and thus pure methanol is obtained. The gas phase obtained in the phase separation device 14 contains non-converted synthesis gas constituents and possibly inert gas constituents. Via conduit 16, cycle compressor 18 and conduit 19 it is recirculated to the second mixing device 6 as synthesis gas cycle gas stream.

Via conduit 17 a part of the synthesis gas cycle gas stream is discharged from the synthesis gas circuit as purge gas stream (purge gas) and guided to the washing device 20. In the washing device the purge gas stream is charged with demineralized water as washing agent, which is supplied via conduit 21. However, other water qualities, in particular those of higher purity, for example high-purity water or distilled water, can also be used as washing agent. Water of lower purity can be used as washing agent when the accompanying substances present create no problems in downstream process stages. Via conduit 22, a purge gas stream reduced in its methanol loading is discharged from the upper region of the washing column, while via conduit 23 the washing agent loaded with methanol is discharged from the lower region of the washing column. The washing agent loaded with methanol is combined with the liquid phase from the phase separation device, which is discharged in conduit 15, and guided to the non-illustrated distillation device.

The purge gas stream reduced in its methanol loading is superheated by means of a non-illustrated heat exchanger, in order to prevent condensation before or in the membrane separation stage, and via conduit 22 guided to the membrane separation stage 24. There, it is fractionated into a permeate stream enriched in hydrogen and a retentate stream depleted of hydrogen. Via conduits 26 and 30, the permeate stream enriched in hydrogen is recirculated to the first mixing device 2 as hydrogen-containing trimming gas stream and thus serves for adjusting the desired stoichiometric number R. The adjustment is made via a non-illustrated flow rate control arranged in the conduit path of conduits 26 and 30. If the hydrogen deficit of the synthesis gas make-up gas stream only is small and not the entire permeate gas stream is required for the adjustment of the desired stoichiometric number, the excess fraction can be discharged from the membrane separation stage via a non-illustrated conduit and for example be utilized as heating gas. It can also be supplied to external consumers, which can process a gas stream with relatively low hydrogen purity.

The retentate stream depleted of hydrogen is discharged from the membrane separation stage via conduit 25 and charged to the pressure swing adsorption stage 27. In the pressure swing adsorption stage a second gas stream enriched in hydrogen is obtained, which is discharged via conduit 29 and together with the permeate stream from the membrane system, which is guided in conduits 26 and 30, is combined as trimming gas stream with the synthesis gas make-up gas stream deficient in hydrogen. When, as explained above, not the entire gas stream enriched in hydrogen from the pressure swing adsorption stage is required for adjusting the desired stoichiometric number, the excess fraction can be discharged from the process as hydrogen export stream via a non-illustrated conduit and be supplied to external consumers.

Via conduit 28, the residual gas stream (PSA tail gas) depleted of hydrogen is discharged from the pressure swing adsorption stage. It still contains combustible components, for example carbon monoxide, and therefore can be utilized for example as heating gas. A material use of the residual gas stream, for example in an adjacent plant for coal gasification, also is possible.

Figure 2:
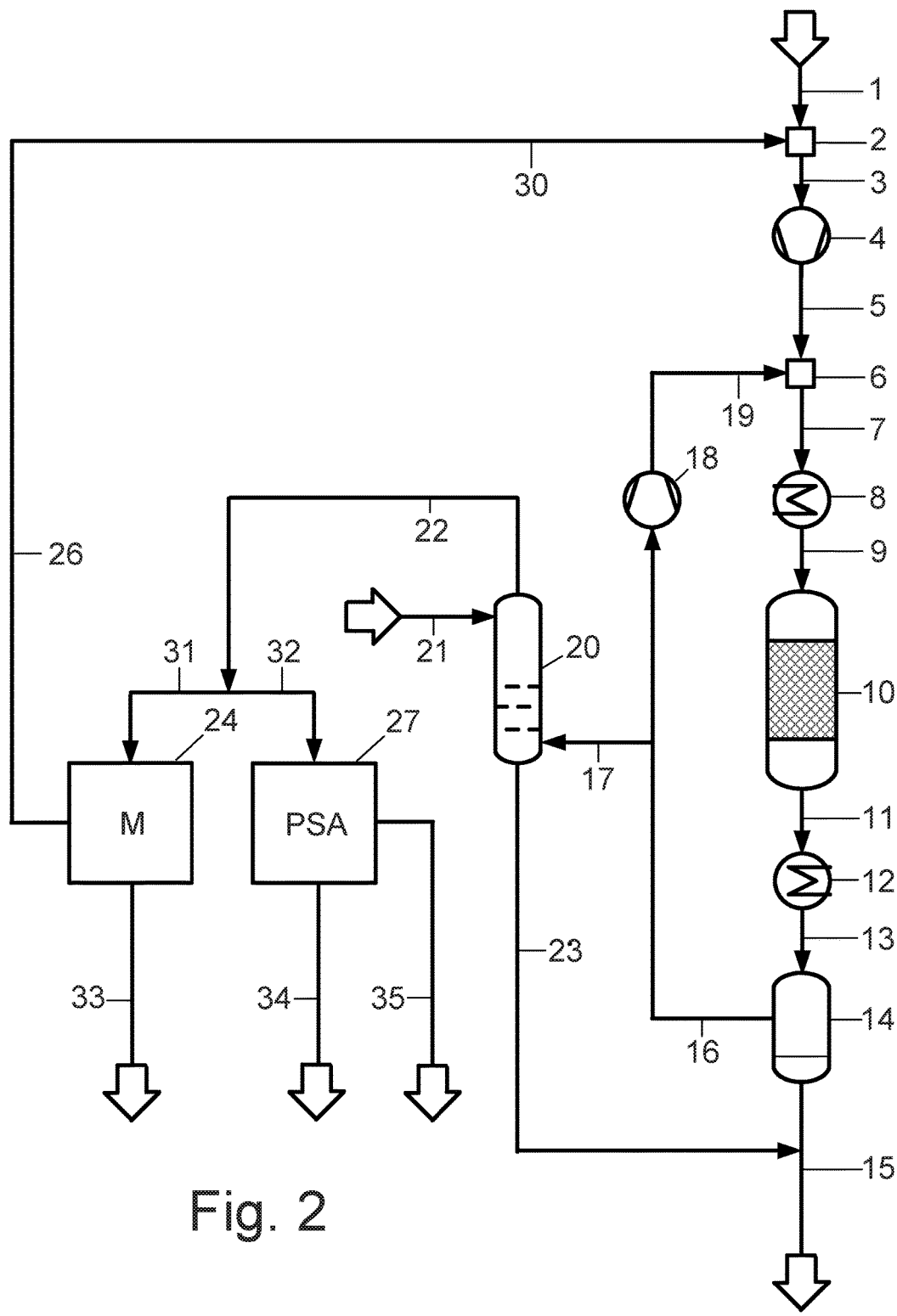
FIG. 2 shows the schematic representation of the process of the invention and the plant of the invention according to a second aspect.

In FIG. 2 the process according to the invention or the plant according to the invention up to reference numeral 23 corresponds to the first aspect discussed above. In contrast to the latter, however, the purge gas stream depleted of methanol, which is supplied via conduit 22, in the second aspect of the invention now is guided in parallel to the membrane separation stage 24 and the pressure swing adsorption stage 27 by means of conduits 31 and 32 and charged to the same. The distribution of the partial gas streams guided to the membrane separation stage 24 and the pressure swing adsorption stage 27 is not necessarily the same; it rather will depend on the quantity of the permeate stream enriched in hydrogen, which is obtained in the membrane separation stage 24 and guided via conduits 26 and 30 and is required for adjusting the stoichiometric number. An equal distribution of the two streams very well is possible and desirable for example when a correspondingly large hydrogen export stream from the pressure swing adsorption stage is to be supplied to external consumers.

The distribution on the two separation stages is performed via non-illustrated flow rate control units arranged in the conduit path of conduits 31 and 32. Via conduits 26 and 30, the permeate stream from the membrane separation stage, which is enriched in hydrogen, is guided to the first mixing device as trimming gas stream and combined there with the synthesis gas make-up gas stream deficient in hydrogen.

Via conduit 35 a pure hydrogen stream with a hydrogen purity of typically more than 99 vol-% is discharged from the pressure swing adsorption stage 27 and supplied to external consumers as export stream.

Via conduits 33 and 34, the retentate stream from the membrane separation stage, which is depleted of hydrogen, and the residual gas stream (PSA tail gas) likewise depleted of hydrogen, is discharged from the pressure swing adsorption stage. Both streams still contain combustible components, for example carbon monoxide, and thus can thermally be utilized with regard to their calorific value, for example in a reformer plant upstream of the methanol synthesis, for undergrate firing of the reformer furnace. A material use of the retentate stream and of the residual gas stream, for example in an adjacent plant for coal gasification, also is possible.

NUMERICAL EXAMPLES

The following numerical examples illustrate the separation of methanol from the purge gas stream (purge gas) loaded with methanol residues in the washing device (Table 1). Furthermore, the separation and recirculation of the hydrogen with a series connection (Table 2) and with a parallel connection (Table 3) of the membrane separation stage and the pressure swing adsorption stage are demonstrated, as they have been explained in the above exemplary embodiments with reference to FIG. 1 and FIG. 2.

The data represented in Tables 2 and 3 illustrate the modes of action and applications of the two described aspects of the invention. With a series connection of membrane separation stage and pressure swing adsorption stage according to FIG. 2 and Table 2 a total amount of 967 kmol/h of hydrogen can be recirculated to the methanol synthesis.

With a parallel connection according to FIG. 2 and Table 3 a total amount of only 361 kmol/h of hydrogen is recirculated to the methanol synthesis, but another 412 kmol/h of high-purity hydrogen are obtained as export stream.

TABLE 1

Separation of methanol from the purge gas stream (purge gas) loaded with methanol residues in the washing device
FIGS. 1 and 2: Purge gas scrubbing

| Mole fractions: | Conduit | | | | |
| --- | --- | --- | --- | --- | --- |
|  | 17 | 21 | 23 | 22 | 22-WT[1] |
| Methanol | 0.006 | 0.000 | 0.046 | 0.000 | 0.000 |
| $H_2O$ | 0.000 | 1.000 | 0.952 | 0.001 | 0.001 |
| $CO_2$ | 0.042 | 0.000 | 0.001 | 0.042 | 0.042 |
| CO | 0.064 | 0.000 | 0.000 | 0.065 | 0.065 |
| $H_2$ | 0.799 | 0.000 | 0.001 | 0.803 | 0.803 |
| Ar | 0.000 | 0.000 | 0.000 | 0.000 | 0.000 |
| $N_2$ | 0.088 | 0.000 | 0.000 | 0.089 | 0.089 |
| $CH_4$ | 0.000 | 0.000 | 0.000 | 0.000 | 0.000 |
| Total stream kmol/h | 1288 | 153 | 159 | 1282 | 1282 |
| Total stream kg/h | 10224 | 2755 | 2968 | 10010 | 10010 |
| Total stream $m^3$/h | 490 | 3 | 3 | 498 | 508 |
| Temperature ° C. | 40 | 42 | 45 | 44 | 50 |
| Pressure MPa, g | 7.0 | 8.1 | 7.0 | 7.0 | 7.0 |

[1]stream in conduit 22 after heating in heat exchanger, not illustrated

TABLE 2

Separation and recirculation of the hydrogen with series connection of membrane separation stage and pressure swing adsorption stage
FIG. 1: Series connection of membrane + PSA

| Mole fractions: | Conduit | | | | |
|---|---|---|---|---|---|
| | 26 | 25 | 28 | 29 | 30 |
| Methanol | 0.000 | 0.000 | 0.000 | 0.000 | 0.000 |
| $H_2O$ | 0.002 | 0.001 | 0.002 | 0.000 | 0.001 |
| $CO_2$ | 0.042 | 0.044 | 0.092 | 0.000 | 0.032 |
| CO | 0.034 | 0.118 | 0.248 | 0.000 | 0.026 |
| $H_2$ | 0.888 | 0.656 | 0.276 | 0.999 | 0.914 |
| Ar | 0.000 | 0.000 | 0.000 | 0.000 | 0.000 |
| $N_2$ | 0.035 | 0.181 | 0.381 | 0.000 | 0.027 |
| $CH_4$ | 0.000 | 0.000 | 0.001 | 0.000 | 0.000 |
| Total stream kmol/h | 811 | 471 | 224 | 247 | 1058 |
| Total stream kg/h | 4524 | 5486 | 4983 | 503 | 5027 |
| Total stream $m^3$/h | 672 | 186 | 2986 | 130 | 905 |
| Temperature ° C. | 50 | 50 | 50 | 50 | 50 |
| Pressure MPa, g | 3.2 | 7.0 | 0.1 | 5.2 | 3.1 |

TABLE 3

Separation and recirculation of the hydrogen with parallel connection of membrane separation stage and pressure swing adsorption stage
FIG. 2: Parallel connection of membrane + PSA

| Mole fractions: | Conduit | | | | | |
|---|---|---|---|---|---|---|
| | 31 | 26 | 33 | 32 | 34 | 35 |
| Methanol | 0.000 | 0.000 | 0.000 | 0.000 | 0.000 | 0.000 |
| $H_2O$ | 0.001 | 0.002 | 0.001 | 0.001 | 0.004 | 0.000 |
| $CO_2$ | 0.042 | 0.042 | 0.044 | 0.042 | 0.119 | 0.000 |
| CO | 0.065 | 0.034 | 0.118 | 0.065 | 0.180 | 0.000 |
| $H_2$ | 0.803 | 0.888 | 0.656 | 0.803 | 0.449 | 1.000 |
| Ar | 0.000 | 0.000 | 0.000 | 0.000 | 0.000 | 0.000 |
| $N_2$ | 0.089 | 0.035 | 0.181 | 0.089 | 0.248 | 0.000 |
| $CH_4$ | 0.000 | 0.000 | 0.000 | 0.000 | 0.001 | 0.000 |
| Total stream kmol/h | 641 | 406 | 235 | 641 | 229 | 412 |
| Total stream kg/h | 5005 | 2262 | 2743 | 5005 | 4171 | 834 |
| Total stream $m^3$/h | 254 | 161 | 93 | 259 | 3062 | 223 |
| Temperature ° C. | 50 | 50 | 50 | 50.0 | 50.0 | 50.2 |
| Pressure MPa, g | 7.0 | 7.0 | 7.0 | 6.8 | 0.1 | 5.0 |

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

INDUSTRIAL APPLICABILITY

With the invention a plant and a process are provided for processing synthesis gas deficient in $H_2$ in the methanol synthesis. As compared to the processes known from the prior art the invention offers the advantage that the hydrogen required for compensating the deficit is obtained from the purge gas of the methanol synthesis and for example not from the synthesis gas make-up gas stream. Therefore, no waste stream containing CO and $CO_2$ is obtained upstream of the methanol synthesis, so that all carbon oxides contained in the make-up gas stream get into the methanol synthesis.

It is particularly favorable when by providing corresponding additional conduits and shut-off members the invention is designed such that the two aspects shown in FIGS. 1 and 2 can be transferred into each other by simple switch-over.

This allows a flexible reaction to the hydrogen deficit of the synthesis gas used and to a changed hydrogen demand of external consumers.

LIST OF REFERENCE NUMERALS 1 conduit
2 first mixing device
3 conduit
4 compressor
5 conduit
6 second mixing device
7 conduit
8 heating device
9 conduit
10 methanol synthesis reactor
11 conduit
12 cooler
13 conduit
14 phase separation device
15-17 conduit
18 cycle compressor
19 conduit
20 washing device
21-23 conduit
24 membrane separation stage (M)
25-26 conduit
27 pressure swing adsorption stage (PSA)
28-35 conduit

The invention claimed is:

1. A process for producing methanol from a synthesis gas comprising hydrogen and carbon oxides, the process comprising the following steps:
   (a) providing a synthesis gas make-up gas stream comprising hydrogen and carbon oxides, wherein the synthesis gas make-up gas stream contains a hydrogen deficit with respect to the stoichiometry specified for methanol synthesis;
   (b) combining the synthesis gas make-up gas stream from step (a) with a trimming gas stream containing hydrogen to obtain a synthesis gas make-up gas stream enriched in hydrogen;
   (c) combining the synthesis gas make-up gas stream enriched in hydrogen with a synthesis gas cycle gas stream obtained in step (g) to obtain a synthesis gas feed gas stream;
   (d) introducing the synthesis gas feed gas stream into at least one methanol synthesis reactor and at least in part catalytically converting the carbon oxides contained in the synthesis gas feed gas stream to methanol by using hydrogen under methanol synthesis conditions;
   (e) discharging a product gas stream containing methanol vapor and non-converted synthesis gas constituents from the at least one methanol synthesis reactor;
   (f) at least partly separating the methanol from the product gas stream by cooling and condensation;
   (g) fractionating the product gas stream after separation of the methanol into the synthesis gas cycle gas stream and a purge gas stream loaded with methanol residues, and recirculating the synthesis gas cycle gas stream to step (c);
   (h) introducing the purge gas stream loaded with methanol residues into a washing device, contacting the purge gas stream loaded with methanol residues in the washing device with a washing agent, and discharging a purge gas stream depleted of methanol and a washing agent loaded with methanol from the washing device;
   (i) introducing the purge gas stream depleted of methanol into a hydrogen separation device which comprises a membrane separation stage and a pressure swing adsorption stage, wherein at least one gas stream enriched in hydrogen and at least one gas stream depleted of hydrogen is obtained; and
   (j) recirculating at least one gas stream enriched in hydrogen as the trimming gas stream containing hydrogen to step (b).

2. The process according to claim 1, wherein in the hydrogen separation device the membrane separation stage and the pressure swing adsorption stage are connected in series and are in fluid connection with each other.

3. The process according to claim 2, wherein in the hydrogen separation device first the membrane separation stage and then the pressure swing adsorption stage are traversed by the purge gas stream depleted of methanol.

4. The process according to claim 3, wherein a first gas stream enriched in hydrogen is obtained as permeate in the membrane separation stage, which as trimming gas stream is combined with the synthesis gas make-up gas stream deficient in hydrogen.

5. The process according to claim 4, wherein the retentate obtained in the membrane separation stage is charged to the pressure swing adsorption stage, and in the pressure swing adsorption stage a second gas stream enriched in hydrogen is obtained, which as trimming gas stream is combined with the synthesis gas make-up gas stream deficient in hydrogen or is discharged from the process as hydrogen export stream.

6. The process according to claim 5, wherein the second gas stream enriched in hydrogen is combined first with the first gas stream enriched in hydrogen and subsequently as trimming gas stream with the synthesis gas make-up gas stream deficient in hydrogen.

7. The process according to claim 1, wherein the membrane separation stage and the pressure swing adsorption stage are connected in parallel in the hydrogen separation device, wherein a part of the purge gas stream depleted of methanol is charged to the membrane separation stage and the remaining part of the purge gas stream depleted of methanol is charged to the pressure swing adsorption stage.

8. The process according to claim 7, wherein a first gas stream enriched in hydrogen is obtained as permeate in the membrane separation stage, which as trimming gas stream is combined with the synthesis gas make-up gas stream deficient in hydrogen.

9. The process according to claim 7, wherein a second gas stream enriched in hydrogen is obtained in the pressure swing adsorption stage, which as trimming gas stream is combined with the synthesis gas make-up gas stream deficient in hydrogen or is discharged from the process as hydrogen export stream.

10. The process according to claim 1, wherein the provision of the synthesis gas make-up gas stream is effected by means of a synthesis gas generation stage which comprises an autothermal reformer.

11. A plant for producing methanol from a synthesis gas containing hydrogen, carbon oxides and optionally inert components, comprising the following plant components:
   (a) a synthesis gas generation stage for providing a synthesis gas make-up gas stream containing hydrogen, carbon oxides and optionally inert components, which contains a hydrogen deficit with respect to the stoichiometry specified for the methanol synthesis,
   (b) a first mixing device for combining the synthesis gas make-up gas stream deficient in hydrogen with a trimming gas stream containing hydrogen to obtain a synthesis gas make-up gas stream enriched in hydrogen,
(c) a second mixing device for combining the synthesis gas make-up gas stream enriched in hydrogen with a synthesis gas cycle gas stream to obtain a synthesis gas feed gas stream,
(d) at least one methanol synthesis reactor, a conduit for introducing the synthesis gas feed gas stream into the at least one methanol synthesis reactor,
(e) a conduit for discharging a product gas stream containing methanol vapor and non-converted synthesis gas constituents from the at least one methanol synthesis reactor,
(f) a separating device for at least partly separating the methanol from the product gas stream by cooling and condensation,
(g) a fractionating device for fractionating the product gas stream after separation of the methanol into a synthesis gas cycle gas stream and a purge gas stream loaded with methanol residues, and a conduit for recirculating the synthesis gas cycle gas stream to the second mixing device,
(h) a washing device, a conduit for introducing the purge gas stream loaded with methanol residues into the washing device, a conduit for introducing the washing agent, a conduit for discharging a purge gas stream depleted of methanol from the washing device, and a conduit for discharging a washing agent loaded with methanol from the washing device,
(i) a hydrogen separation device, comprising a membrane separation stage and a pressure swing adsorption stage, a conduit for introducing the purge gas stream depleted of methanol into the hydrogen separation device, a conduit for discharging a gas stream enriched in hydrogen from the hydrogen separation device, and a conduit for discharging a gas stream depleted of hydrogen from the hydrogen separation device,
(j) a conduit for recirculating a gas stream enriched in hydrogen as trimming gas stream containing hydrogen to the first mixing device.

12. The plant according to claim 11, wherein in the hydrogen separation device the membrane separation stage and the pressure swing adsorption stage are connected in series and are in fluid connection with each other.

13. The plant according to claim 12, wherein in the hydrogen separation device first the membrane separation stage and then the pressure swing adsorption stage are traversed by the purge gas stream depleted of methanol.

14. The plant according to claim 13, further comprising a conduit with which a first gas stream enriched in hydrogen, which is obtained as permeate in the membrane separation stage, is recirculated to the first mixing device as trimming gas stream.

15. The plant according to claim 14, further comprising a conduit for introducing the retentate obtained in the membrane separation stage into the pressure swing adsorption stage and a conduit for introducing a second gas stream enriched in hydrogen, which is obtained in the pressure swing adsorption stage, as trimming gas stream into the first mixing device or for discharging from the plant as hydrogen export stream.

16. The plant according to claim 15, further comprising a mixing device for combining the second gas stream enriched in hydrogen with the first gas stream enriched in hydrogen, and a conduit for supplying the mixed gas stream obtained to the first mixing device.

17. The plant according to claim 11, wherein the membrane separation stage and the pressure swing adsorption stage are connected in parallel in the hydrogen separation device, and furthermore comprising a conduit for introducing a part of the purge gas stream depleted of methanol into the membrane separation stage and a conduit for introducing the remaining part of the purge gas stream depleted of methanol into the pressure swing adsorption stage.

18. The plant according to claim 17, further comprising a conduit with which a first gas stream enriched in hydrogen, which is obtained as permeate in the membrane separation stage, is recirculated to the first mixing device as trimming gas stream.

19. The plant according to claim 18, further comprising a conduit for introducing a second gas stream enriched in hydrogen, which is obtained in the pressure swing adsorption stage, as trimming gas stream into the first mixing device or for discharging from the plant as hydrogen export stream.

* * * * *